United States Patent [19]
Webster

[11] Patent Number: 6,127,605
[45] Date of Patent: Oct. 3, 2000

[54] **STARCHLESS VARIETY OF *PISUM SATIVUM* HAVING ELEVATED LEVELS OF SUCROSE**

[75] Inventor: David Webster, Buhl, Id.

[73] Assignee: Seminis Vegetable Seeds, Inc., Saticoy, Calif.

[21] Appl. No.: 09/015,711

[22] Filed: Jan. 29, 1998

Related U.S. Application Data

[63] Continuation-in-part of application No. 08/986,616, Dec. 8, 1997, abandoned.
[51] Int. Cl.$^7$ .............................. A01H 5/00; A01H 5/10; A01H 1/04
[52] U.S. Cl. ........................ 800/298; 800/260; 800/263; 800/265
[58] Field of Search ..................................... 800/263, 260, 800/298, 265

[56] References Cited

U.S. PATENT DOCUMENTS

| | | | |
|---|---|---|---|
| 5,286,635 | 2/1994 | Hanson et al. | 435/172.3 |
| 5,498,831 | 3/1996 | Burgess et al. | 800/205 |
| 5,646,023 | 7/1997 | Secor et al. | 435/172.3 |
| 5,705,375 | 1/1998 | Van Ooyen et al. | 435/172.3 |

FOREIGN PATENT DOCUMENTS

WO 98/01574  1/1998  WIPO .

OTHER PUBLICATIONS

Harrison, C.J. et al., "Evidence that rug3 locus of pea (Pisum sativum L.) encodes plastidial phosphoglucomutase confirms that the imported substrate for starch synthesis in pea amyloplasts is glucose–6–phosphate", *The Plant Journal*, 13(6):753–762, (1998).

International Preliminary Report for PCT/US98/25912 (1999).

Wang, T.L. et al., *IPSR & JIC Annual Report*, (1992).

Peas: Genetics, Molecular Biology and Biotechnology 5. Genetic and Developmental Analysis of the Seed; Edited by Casey R., Davis D.R., pp. 83–120 (1993) ISBN–0–85198–863–6.

Wang, T.L. et al., *Seed Science Research*, 1:3–14, (1991).

Wang, T.L. et al., *Plant Breeding*, 105:311–320, (1990).

Basterrechea et al. Effect of maturity on carbohydrate changes in sugar snap pea pods during storage. Scientia Horticulturae. vol. 48, No. 1–2, pp. 1–8, 1991.

Gaze et al. Suitability of the ottawa pea tenderometer to assess the quality of raw peas. Journal of Food Technology. vol. 21, Nol 3, 319–330, 1986.

*Primary Examiner*—Lynette R. F. Smith
*Assistant Examiner*—Melissa L. Kimball
*Attorney, Agent, or Firm*—Rockey, Milnamow & Katz, Ltd.

[57] ABSTRACT

The present invention relates to a *Pisum sativum* variety that contains a recessive gene called the *bsg* gene and produces peas that exhibit an elevated level of sucrose and a decreased level of alcohol insoluble solids when compared to peas produced from a *Pisum sativum* variety that does not contain the *bsg* gene within its genome.

23 Claims, 5 Drawing Sheets

6,127,605

STARCHLESS VARIETY OF *PISUM SATIVUM* HAVING ELEVATED LEVELS OF SUCROSE

RELATED APPLICATION INFORMATION

This application is a continuation-in-part of U.S. application Ser. No. 08/986,616, filed on Dec. 8, 1997 now abandoned.

TECHNICAL FIELD OF THE INVENTION

The present invention relates to a *Pisum sativum* variety that contains a recessive gene that produces highly wrinkled seed having a low starch content.

BACKGROUND OF THE INVENTION

The garden pea (*Pisum sativum* L.) is a commercially important food crop and the immature seed of the garden pea ("peas") are widely consumed. There are a large number of genes that affect peas. The first reported and best described gene is the *r* gene (see White, O. E., *Proceedings of the American Philosophical Society*, 56: 487–588). The *r* mutant is believed to have occurred spontaneously at the beginning of the seventeenth century (see Lamprecht, H., *Agri. Hortique Genetica* 14: 1–4 (1956)) and its mature, dry seed has a wrinkled appearance (hence "*r*", derived from the Latin, rugosus meaning "wrinkled or shriveled"). Wrinkling of mature seed was one of the characteristics used by Mendel in experiments which led him to formulate his laws of inheritance. (see Mendel, G., *Verhandlungen des naturforshenden Vereinds in Brünn* 4: 3–47 (1865)). A second gene, referred to as *rb*, has also been identified. Mature seeds homozygous for *rb* also exhibit a wrinkled appearance.

Genes at the rugosus loci, *R* and *Rb*, are known to affect the development of embryos directly in peas. (see Wang, T. L., et al., *Plant Breeding* 105: 311–320 (1990)). The *R* locus has been shown to encode one form of the starch branching enzyme. Id. Genes at the *R* and *Rb* loci are pleiotropic, affecting the level and type of starch, other storage products, the osmotic environment of the embryo and the growth of the embryo. (see Wang, T. L., et al., "*New Mutants for Seed Development in Peas*" in IPSR & JIC Annual Report (1992)).

Sweetness, such as sucrose content, in peas, is generally prized by consumers, who perceive that sweeter peas have a better flavor. Thereupon, because peas are such an important food crop, there is a need in the art for peas having an increased sweetness.

SUMMARY OF THE INVENTION

The present invention relates to a new variety of *Pisum sativum*, which is resistant to Fusarium Wilt Fungus and Powdery Mildew Fungus and which contains within its genome, a homozygous recessive gene, referred to as the *bsg* gene. A *Pisum sativum* variety that contains the *bsg* gene within its genome produces peas (known in the art as immature seeds) which exhibit an elevated level of sucrose and a decreased level of alcohol insoluble solids when compared with peas produced from a *Pisum sativum* variety that does not contain the *bsg* gene homozygous within its genome.

The peas of the present invention contain from about 6.0 to about 7.5 percent fresh weight of sucrose when measured at a tenderometer value of from about 90 to about 110 and from about 6.5 to about 8.0 percent by weight of alcohol insoluble solids when measured at a tenderometer value of about 105. Moreover, the peas of the present invention contain from about 5 to about 30 percent fresh weight more sucrose than peas produced from a *Pisum sativum* variety that does not contain the *bsg* gene homozygous within its genome. Additionally, the peas of the present invention exhibit twenty (20) percent less alcohol insoluble solids when compared with peas from a *Pisum sativum* that does not contain the *bsg* gene homozygous within its genome.

Additionally, the present invention relates to a process for producing peas of a *Pisum sativum* variety that contain higher levels of sucrose and lower levels of alcohol insoluble solids than peas from a *Pisum sativum* variety that does not contain the *bsg* gene homozygous within its genome. The process involves crossing a *Pisum sativum* variety or line that contains the *bsg* gene homozygous within its genome with a second *Pisum sativum* variety or line that contains the *bsg* gene homozygous within its genome, collecting the resulting mature seeds, planting the mature seeds, growing the mature seeds into *Pisum sativum* plants, selecting *Pisum sativum* plants with desirable phenotypic traits; allowing the plants to self-pollinate until a uniform line is produced, allowing the *Pisum sativum* line to self-pollinate, and collecting the resulting peas.

In another embodiment, the process involves crossing a *Pisum sativum* variety or line that contains the *bsg* gene homozygous within its genome with a second *Pisum sativum* variety or line which does not contain the *bsg* gene within its genome, collecting dry, mature seeds, planting the collected dry, mature seeds, growing the mature seeds into *Pisum sativum* plants, allowing the plants to self-pollinate, collecting the resulting dry, mature seeds, selecting highly wrinkled mature seeds that do not contain organized starch grains and which do not stain purple when treated with a solution of iodine and potassium iodide, planting said highly wrinkled mature seeds, growing the mature seeds into *Pisum sativum* plants, selecting plants with desirable phenotypic traits, allowing the plants to self-pollinate until a uniform *Pisum sativum* line is produced, allowing the *Pisum sativum* line selected to self-pollinate, and collecting the resulting peas. The *Pisum sativum* variety or line that does not contain the *bsg* gene within its genome can contain any combination of the genes such as the *r, rb, R* or *Rb* homozygous within its genome. The peas produced by the process of the present invention contain from about 6.0 to about 7.5 percent fresh weight of sucrose when measured at a tenderometer value of from about 90 to about 110 and from about 6.5 to about 8.0 percent by weight of alcohol insoluble solids when measured at a tenderometer value of about 105.

The present invention also contemplates a process of producing highly wrinkled mature seed of a *Pisum sativum* variety that contains the *bsg* gene within its genome. In one embodiment the process involves crossing a *Pisum sativum* variety or line that contains the *bsg* gene within its genome with a second *Pisum sativum* variety or line that contains the *bsg* gene within its genome and collecting the resulting mature seeds.

In another embodiment, the process involves crossing a *Pisum sativum* variety or line that contains the *bsg* gene within its genome with a *Pisum sativum* variety or line that does not contain the *bsg* gene within its genome, collecting mature seeds, planting the collected mature seeds, growing the mature seeds into *Pisum sativum* plants, allowing the plants to self-pollinate, collecting mature seeds, selecting highly wrinkled seeds that do not contain organized starch grains, planting said mature seeds and growing the seeds into *Pisum sativum* plants, selecting plants with desirable phenotypic traits, allowing the plants to self-pollinate until a uniform *Pisum sativum* line is produced, allowing the *Pisum sativum* line to self-pollinate and collecting the mature seeds.

The present invention also contemplates *Pisum sativum* varieties grown from the mature seed described above and peas harvested from said varieties.

BRIEF DESCRIPTION OF THE DRAWINGS

FIG. 1 shows starch granules from three different types of dry, mature *Pisum sativum* seeds.

DETAILED DESCRIPTION OF THE INVENTION

The present invention relates to a novel garden variety of pea, *Pisum sativum*, that contains within its genome, a homozygous recessive gene, referred to as "*bsg*" (*bsg* referring to "blown starch grain"). As used herein, the term "genome" refers to the entire hereditary material (DNA) in a cell which is composed of one or more chromosomes.

It is well known in the art that peas are the immature seeds of a *Pisum sativum* variety. Peas or immature seeds typically do not exhibit a wrinkled appearance. Peas or immature seeds are consumed by individuals as food. Mature seeds of a *Pisum sativum* variety are dry seeds. Mature seed exhibits a wrinkled appearance if it contains the *r* or *rb* genes or *bsg* gene within its genome. Mature seeds are used for planting and produce *Pisum sativum* varieties.

The *Pisum sativum* variety of the present invention contains a homozygous *bsg* gene within its genome and produces mature seeds which are highly wrinkled and have a very low starch content. The mature seeds of the present invention also contain a homozygous *bsg* gene within their genome and contain few, if any, organized starch granules when examined under a microscope. Instead of containing starch granules, mature seeds of the present invention contain granular material of unknown composition.

Figure 1A:
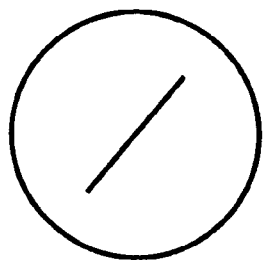
FIG. 1a shows the starch granules from a smooth or an alsweet seed which contain the *R* gene homozygous within its genome.
Figure 1B:
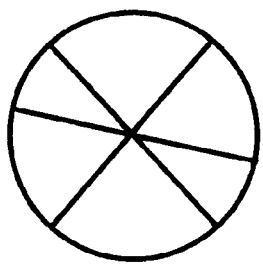
FIG. 1b shows the starch granules from a wrinkled seed which contains a *r* gene homozygous within its genome.
Figure 1C:
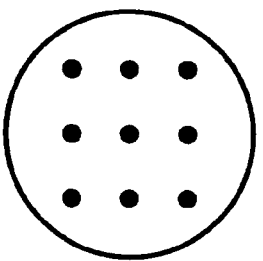
FIG. 1c shows the near absence of starch granules and the presence of granular material of unknown composition in mature seed containing a homozygous *bsg* gene.
Figure 2:
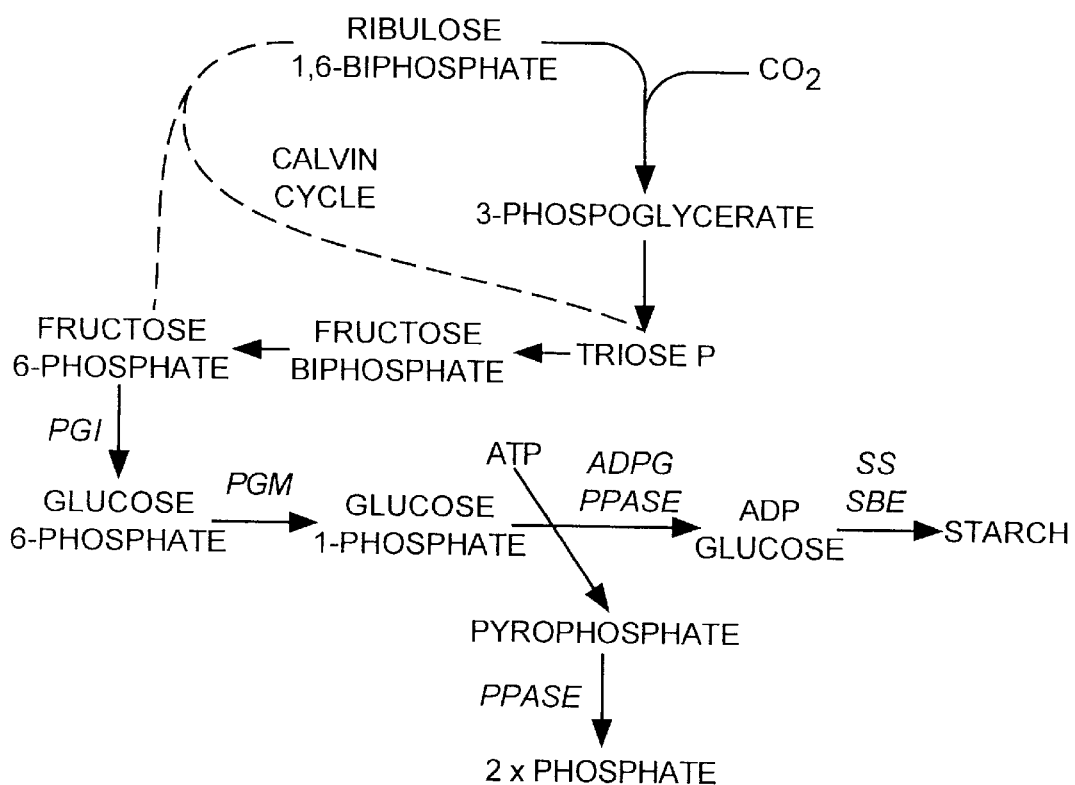
FIG. 2 shows starch biosynthesis in a chloroplast.
Figure 3:
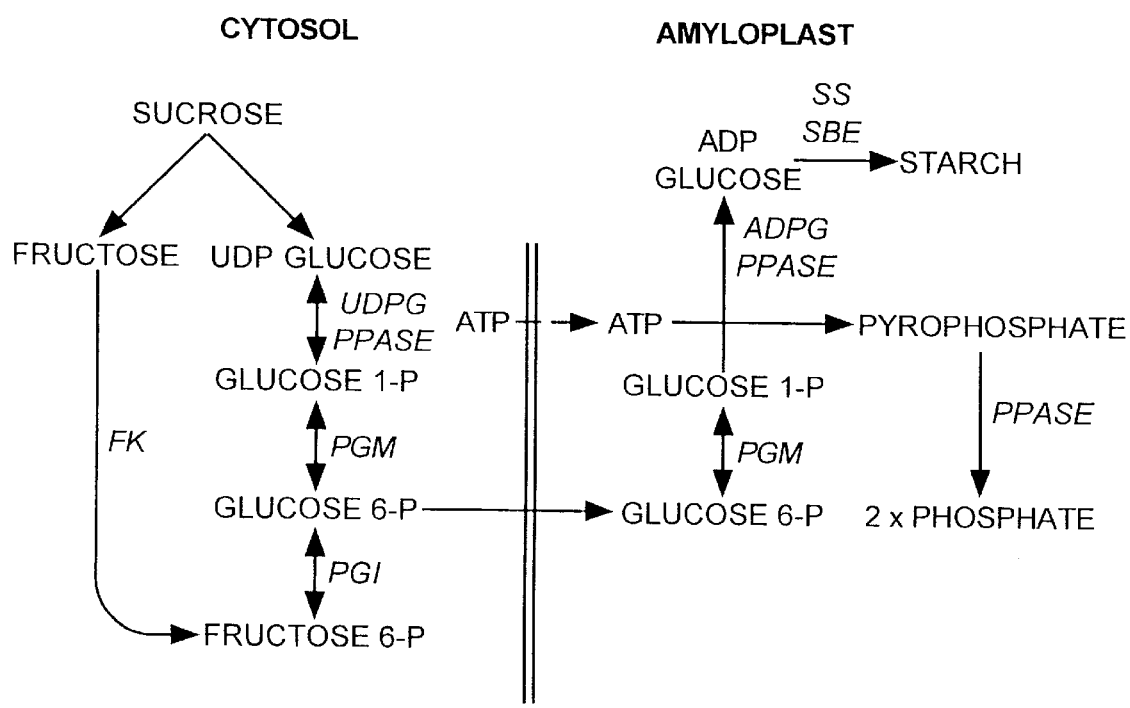
FIG. 3 shows starch biosynthesis in an amyloplast.

FIG. 1 demonstrates the appearance under a microscope of starch granules in various types of mature *Pisum sativum* seeds. FIG. 1a shows the appearance of starch granules in smooth or alsweet mature seeds that contain the *R* gene homozygous with their genome. These mature seeds have entire starch granules and do not contain the *r* or *bsg* genes homozygous within their genome. FIG. 1b shows the appearance of the starch granules in a wrinkled mature seed that contains the *r* gene homozygous within its genome. The starch granules in the wrinkled mature seed containing the *r* gene homozygous exhibit a star shaped fracture pattern similar to that of a pie that has been scored into 5 or 6 pieces. FIG. 1c shows mature seed of the present invention that contains the *bsg* gene homozygous within its genome. As shown in FIG. 1c, mature seeds of the present invention contain few, if any, organized starch granules but instead contain granular material. When the mature seeds shown in FIG. 1c are treated with a solution of iodine and potassium iodide, the mature seeds fail to stain purple due to the near absence of starch.

Due to the absence of starch, the *Pisum sativum* variety of the present invention also produces the peas or immature seeds that contain elevated levels of sucrose. As used herein, the term "sucrose" refers to the disaccharide composed of glucose and fructose.

The peas of the present invention contain the *bsg* gene homozygous within their genome and further contain from about 6.0 to about 7.5, preferably from about 6.2 to about 7.1 percent fresh weight of sucrose when measured at a tenderometer value of from about 90 to about 110. A tenderometer is a device that is used to measure the tenderness of peas, beans and broad beans. As used herein, the term "tenderometer value" refers to a measure of the force required to crush about 200 grams of peas using a tenderometer. Higher tenderometer values indicates more advanced maturity of the peas. Processed green peas are typically harvested at tenderometer values of from 90 to 120.

The peas of the present invention contain from about 5 to about 30 percent fresh weight, preferably from about 10 to about 20 percent fresh weight, more sucrose than peas produced from a *Pisum sativum* variety that does not contain the *bsg* gene homozygous within its genome, particularly wrinkled varieties of peas. As used herein, the term "wrinkled varieties of peas" refers to *Pisum sativum* that contain a homozygous *r* (rugosus) or homozygous *rb* gene within their genome, so that the appearance of the mature seed is wrinkled. Quantum is the sweetest variety of pea that is known by the inventor that contains the *r* gene homozygous within its genome. Quantum is commercially available under the Asgrow Brand, from Seminis Vegetable Seeds, Inc., the assignee of the present invention. Quantum peas contain from about 5.0 to about 6.2 percent fresh weight of sucrose.

Additionally, the peas of the present invention exhibit a depressed level of alcohol insoluble solids (AIS). High AIS correlates with decreased product quality. The peas of the present invention contain from about 6.5 to about 8.0, preferably from about 7.0 to about 7.5 percent by weight of alcohol insoluble solids when measured at a tenderometer value of about 105. Moreover, the peas of the present invention exhibit about twenty (20) percent less AIS than peas from a *Pisum sativum* variety that does not contain the *bsg* gene homozygous within its genome (such as wrinkled varieties of peas). For example, peas of the present invention contain about twenty (20) percent less AIS than the peas produced by the variety Quantum.

Furthermore, the mature seeds of the present invention contain very little starch. More specifically, the seeds of the present invention contain from about 0.01 to 3.0 percent dry weight, preferably, from about 0.5 to 2.0 percent dry weight of starch.

The *Pisum sativum* variety of the present invention containing a homozygous *bsg* gene within its genome was developed as follows. In 1990, a wrinkled-seed mutant was discovered in a crop of Frimousse, which is a smooth-seed *Pisum sativum* variety that has no block in the conversion of sugar to starch. This crop had been grown at a breeding station in Twin Falls, Id. This single mutant was discovered when the crop was undergoing seed-uniformity tests. Frimousse is commercially available under the Asgrow Brand, from Seminis Vegetable Seeds, Inc. Seed of this wrinkle-seed mutant was then crossed with the *Pisum sativum* variety Encore in a greenhouse in Twin Falls, Id. Encore is a full season, large sieve commercial *Pisum sativum* variety with dark green (freezer) berry color, good processed quality, and resistance to Powdery Mildew Fungus and Race 1 of the Fusarium Wilt Fungus. Dry, mature seed of Encore is available under the Asgrow Brand from Seminis Vegetable Seeds. One selection that resulted from this cross contained very little starch and was labeled M82.1.

In December 1991, seed of M82.1 and the variety Lazor were planted in a greenhouse in Twin Falls, Id. A cross was made between M82.1 and Lazor. Lazor is a late-season, large sieve *Pisum sativum* variety with dark green berry color and good processed quality and is resistant to Powdery Mildew Fungus and Race 1 of Fusarium Wilt Fungus. Dry, mature seed of Lazor is commercially available under the Asgrow brand from Seminis Vegetable Seeds, Inc., the assignee of the present invention. The resulting mature seed was collected and coded "BC0". In May 1992, seed of BC0 and Lazor were planted in the greenhouse described above and crossed. The resulting mature seed was collected and coded "BC1". In September 1992, seed of BC1 and Lazor were planted in the greenhouse described above and crossed. The resulting mature seed was collected and coded "BC2F1". In February 1993, seed of BC2F1 were planted in the same greenhouse and allowed to self-pollinate. The resulting mature seeds were collected and coded "BC2F2". In April 1993, several BC2F2 seeds that did not contain any organized starch grains were selected.

Later in 1993, the BC2F2 seeds selected above were then planted in a field in Twin Falls, Id. From the resulting population, individual lines containing the best horticultural characteristics were then selected and allowed to self-pollinate. Selection criteria included uniform emergence, short erect variety type, productivity and uniformly of pod set. The resulting mature seeds were collected and coded "BC2F3". In April 1994, BC2F3 seed was planted in Twin Falls, Id.

From the resulting population, individual lines exhibiting the best horticultural characteristics were selected and allowed to self-pollinate. The resulting seed was collected and coded "BC2F4". In April 1995, BC2F4 seed was planted under the code name "R954593" in Twin Falls, Id. Observations made during the growing season indicated that the line was uniform and bred true. The resulting variety was allowed to self-pollinate and the resulting seed was collected and coded 8500017. In winter 1995, the 8500017 seed was planted in Guatemala and the resulting seed bulked for further trialing and increase.

Mature seeds of 8500017 developed as a result of the above breeding have been deposited under the Budapest Treaty with the American Type Culture Collection (hereinafter "ATCC"), 10801 University Blvd., Manassas, Va. 20110-2209 on Nov. 3, 1997 and have received accession number 209425. This deposit of 8500017 was made under the Budapest Treaty and will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has satisfied all the requirements of 37 C.F.R. Sections 1.801–1.809, including providing an indication of the viability of the sample. Furthermore, a Plant Variety Protection Certificate has been applied for with the United States Department of Agriculture.

The present invention also contemplates a process for developing *Pisum sativum* varieties that produce peas that contain higher levels of sucrose than peas produced by a *Pisum sativum* variety that does not contain the *bsg* gene within its genome. In one embodiment, the process involves crossing a *Pisum sativum* variety or line that contains the *bsg* gene homozygous within its genome with a second *Pisum sativum* variety or line that also contains the *bsg* gene homozygous within its genome, collecting the resulting mature seed, planting the mature seed, growing the mature seed into *Pisum sativum* plants, selecting *Pisum sativum* plants with desirable phenotypic traits, allowing the selected plants to self-pollinate until a uniform line is produced, allowing the Pisum sativum line to self-pollinate, and collecting the resulting peas.

In another embodiment, the process involves crossing a *Pisum sativum* variety or line that contains the *bsg* gene within its genome with a second *Pisum sativum* variety or line that does not contain the *bsg* gene within its genome and collecting the resulting mature seed. The *Pisum sativum* variety or line that does not contain the *bsg* gene within its genome can instead contain other genes or combination of genes within its genome. For example, the variety or line may contain the *r* or *rb* gene, or both, which produces wrinkled seed, or the *R* gene which produces smooth seed. The collected mature seed contains the *bsg* gene heterozygous within its genome. The collected mature seed are planted and allowed to grow. The *Pisum sativum* plants grown from said seed are allowed to self-pollinate. As a result of the self-pollination, the plants produce various types of dry, mature seeds that have different genes within their genomes. One type of mature seed that is produced is highly wrinkled. This seed contains virtually no organized starch grains and does not stain purple when treated with a solution of iodine and potassium iodine solution. This mature seed contains the *bsg* gene homozygous within its genome. The mature seed containing the *bsg* gene is selected, collected and planted. *Pisum sativum* plants having desirable phenotypic traits are selected and allowed to self-pollinate until a uniform *Pisum sativum* line is produced. The uniform line is allowed to self-pollinate and the resulting peas collected.

As used herein, the term "line" means a population of genetically and phenotypically similar seeds or plants.

As used herein, the term "uniform *Pisum sativum* line" means a population of genetically and phenotypically similar seeds or plants that may be reproduced by bulk increase without altering the descriptive characteristics of the population. A variety is a uniform that is increased for commerce.

The present invention also contemplates peas produced by any of the hereinbefore described processes. Peas produced pursuant to the above-mentioned processes contain from about 6.0 to about 7.5, preferably from about 6.5 to about 7.0 percent fresh weight sucrose when measured at a tenderometer value of from about 90 to about 110 and from about 6.5 to about 8.0, preferably from about 7.0 to about 7.5 percent by weight alcohol insoluble solids when measured at a tenderometer value of about 105. Moreover, peas produced by the process of the present invention also contain higher levels of sucrose than peas produced from a *Pisum sativum* variety that does not contain the *bsg* gene homozygous within its genome. Moreover, peas produced according to the process of the present invention contain from about 5 to about 30 percent fresh weight, preferably from about 10 to about 20 percent fresh weight, more sucrose than peas produced by a *Pisum sativum* variety that does not contain the *bsg* gene within its genome. Additionally, peas produced according to the process of the present invention contain about twenty (20) percent less AIS than peas produced from a *Pisum sativum* variety that does not contain the *bsg* gene within its genome.

The present invention also contemplates a process for producing highly wrinkled mature seed of a *Pisum sativum* variety that contains the *bsg* gene homozygous within its genome. In one embodiment, the process involves crossing a *Pisum sativum* variety or line that contains the *bsg* gene homozygolus within its genome with a second *Pisum sativum* variety or line that contains the *bsg* gene homozygous within its genome and collecting the resulting mature seeds. The present invention also contemplates *Pisum sativum* varieties grown from said dry, mature seed and peas harvested from said varieties.

In a second embodiment, the process involves crossing a *Pisum sativum* variety or line that contains the *bsg* gene homozygous within its genome with a second *Pisum sativum* variety or line that does not contains the *bsg* gene homozygous within its genome and collecting the resulting mature seeds. After the mature seed is collected, it is planted and grown into plants which are allowed to self-pollinate. The resulting mature seed is collected and highly wrinkled mature seeds that do not contain any organized starch grains are selected. These mature seeds are planted and allowed to grow into *Pisum sativum* plants. *Pisum sativum* plants having desirable phenotypic traits are selected. These selected plants are allowed to self-pollinate until a uniform *Pisum sativum* line is produced. The uniform line is allowed to self-pollinate and mature seeds collected. The present invention also contemplates *Pisum sativum* varieties grown from said dry, mature seed and peas harvested from said varieties.

The following Examples illustrate the preferred embodiments of the present invention and are not limiting of the specification and claims in any way.

EXAMPLE 1

Characteristics of 8500017

Pea cultivar 8500017 has the following characteristics:
Maturity:
  Number of Nodes at first bloom: 15
  The variety of the present invention blooms 5 days later than Wando. Wando is publically available from the Pisum Plant Introduction Collection, USDA ARF, Johnson Hall, Room 55, Washington State University, Pullman, Wash.
  Number of days to procuring: 77
  Host Units: 1630
Height:
  The variety of the present invention is about 45 cm high, and is about 5 cm shorter than Wando.
Vine:
  Habit: Indeterminate
  Branching: 1–2 Branches
  Internodes: Zig Zag
  Stockiness: Slim
  Number of Nodes: 19
Leaflets:
  Color: Dark Green
  Wax: Light
  Marbled: Yes
  Number of leaflet pairs: Two
Stipules:
  The variety of the present invention contains stipules that are marbled. The stipules are the same color as the leaflets, are clasping and are larger in size when compared to the leaflets.
Flower color:
  Venation: Greenish
  Standard: White
  Wing: White
  Keel: White
Pods:
  Shape: Slightly Curved
  Color: Medium Green
  Surface: Rough
  Length: 8 cm
  End: Blunt
  Width (Between Sutures): 11 mm
  Number of Seeds per Pod: 9
Peas: (95–100 Tenderometer)
  Color: Dark Green
    1–5%
    2–17%
    3–35%
    4–39%
    5–4%
    Average: 3.20%
Seeds: (Dry, Mature):
  Shape: Flattened
  Surface: Wrinked and Dull
  Color Pattern: Monocolor
  Primary Color: Cream & Green
  Hilum Floor Color: Tan
  Cotyledon Color: Green
  Number of grams per 100 Seeds: 14
Disease Resistance:
  The *Pisum sativum* variety of the present invention is resistant to Fusarium Wilt Fungus and Powdery Mildew Fungus The closest *Pisum sativum* varieties to the *Pisum sativum* variety of the present invention are: Lazor, Markado and Trek. Lazor has been described earlier. Markado is a full season, medium sieve, freezer with dark green (freezer) peas and with relatively fine foliage compared to other larger sieve freezer varieties. Markado is commercially available from Novartis (Boise, Id.). Trek is a mid-season, medium-sieve freezer variety with afila foliage and medium dark green berry color. Trek is commercially available under the Asgrow Brand from Seminis Vegetable Seeds.

EXAMPLE 2

Starch and Sucrose in the Leaves of the Peas Present Invention and Examination of Enzyme Activity Compared with Peas of a Wrinkled *Pisum sativum* Variety that Contains the *r* Gene.

The pea variety Lazor, which contains homozygous *r* gene and produces wrinkled mature seed, and a *bsg*- introgressed line of Lazor which produces highly wrinkled seed were studied in this example. A sample of leaves from Lazor and *bsg*-introgressed line of Lazor were dried to a stable weight in a lyophilizer and then pulverized to a powder using a mortar and pestle. Pre-weighed amount of the samples (~100 mg) was washed several times in 80% ethanol at 70° C. The ethanol supernatants were pooled and used for sucrose determination. The pellet was used for starch determination.

Quantification of Starch

Sugar was removed from lyophilized tissue samples by several washes at 70° C. in 80% ethanol. Starch was gelatinized by autoclaving for 45 minutes and then hydrolyzed by digestion at 37° C. with α-amylase (Sigma) in 0.3 M sodium acetate, pH 5.2 followed by further digestion with *Aspergillus niger* amyloglucosidase (Sigma) in 0.1 M sodium acetate, pH 4.6 at 55° C. Samples were deproteinized by boiling and glucose was assayed enzymatically by coupling the oxidation of glucose to the reduction of NAD+ with hexokinase (Boehringer/Mannheim) and glucose-6-P dehydrogenase (Sigma).

An aliquot of the hydrolyzed starch was incubated at room temperature in 0.1 M Tris-Cl (pH 8), 1 mM ATP, 1 mM NAD+, 2 mM $MgCl_2$, 15 U/ml yeast hexokinase, and 15 U/ml *Leuconostoc mesenteroides* glucose-6-phosphate dehydrogenase. The reaction was allowed to go to completion and the absorbance was read at 340 nm and compared with a standard curve. The results are shown below in Table 1.

Quantification of Sucrose

The pooled 80% ethanol supernatants were brought to 6.5 mls with 80% ethanol. Following the addition of 3.6 ml of water and 2.15 ml of chloroform, the sample was vortexed and spun in a table top centrifuge. After the bottom phase had been back-extracted with 0.2 ml of water, the top phases were pooled, evaporated to dryness on a Savant Speed-Vac Concentrator, and resuspended in 0.2 ml of water.

Glucose and fructose were destroyed by treating the sample for 30 minutes at 90° C. in the presence of 3.7 volumes of 0.1 M NaOH. The sample was then neutralized by the addition of 0.5 volumes of 1 M sodium acetate, pH 4.6. Sucrose levels were determined using a dehydrogenase-coupled spectrophotometric assay. An aliquot of the alkali-treated sample was incubated at room temperature in 40 mM imidazole (pH 6.9), 1 mM ATP, 1 mM NAD+, 5 mM $MgCl_2$, 0.5 mM DTT, 0.02% BSA, 32 U/ml invertase, 5 U/ml yeast hexokinase, and 5 U/ml *Leuconostoc mesenteroides* glucose-6-phosphate dehydrogenase. The reaction was allowed to go to completion and the absorbance was read at 340 nm and compared with a standard curve. The results are shown below in Table 2.

Table 2 shows that leaf starch levels in the *Pisum sativum* line having the *bsg* gene introgressed into Lazor are at most only about 0.5% of Lazor. Also, Table 2 demonstrates that sucrose levels were increased in the leaves of the *Pisum sativum* line containing the *bsg* gene.

ADP-glucose Pyrophosphorylase Assays

Embryos from Lazor and a *bsg* gene introgressed line of Lazor frozen in liquid nitrogen were ground in a mortar in the presence of 3–4 volumes of ice-cold extraction buffer (100 mM 2-(N-morpholino) ethane sulfonic acid (MOPS) (pH 7.2), 5 mM $MgCl_2$, 1 mM EDTA, 5 mM DTT). Starch and cell debris were removed by pelleting for 10 minutes at 27,000×g. Aliquots of the supernatant were then quick-frozen in liquid nitrogen and stored at −80° C. ADPG-PPase activity was found to be stable under these storage conditions.

ADP-glucose pyrophosphorylase was assayed in the reverse direction at 25° C. by coupling production of glucose-1-P to reduction of NAD+. Standard reaction mixtures (1 ml) contained 75 mM 4-(2-hydroxyethyl)-1-piperazine-ethane sulfonic acid (HEPES) (pH 7.75), 5 mM $MgCl_2$, 1 mM 3PGA, 0.1 mg/ml bovine serum albumin, 5 μM glucose-1,6-bisphosphate; 1.5 mM ADP-glucose, 0.4 mM NAD+; 2 U each of phosphoglucomutase (Sigma) and *Leuconostoc mesenteroides* glucose 6-phosphate dehydrogenase (Sigma), and up to 100 μl of extract. After a one minute pre-incubation period reactions were initiated by addition of sodium pyrophosphate to 1.5 mM. NADH production was monitored spectrophotometrically at 340 nm against a reaction mixture which lacked sodium pyrophosphate. The rate was proportional to the amount of extract added and the reaction was linear over at least 3 minute time periods. One unit is defined as the amount of enzyme that produces 1μ mole of glucose-1-P per minute.

Protein concentrations were determined using the dye reagent from BioRad. The results are shown below in Table 2.

TABLE 2

ADP-glucose pyrophosphorylase Activity in Embryos from Lazor and *bsg*-introgressed lines of *Pisum sativum*

|  | Embryo wt, g | ADPG-PPase activity, U/mg protein |
|---|---|---|
| Lazor | .28 | .0559 |
|  | .31 | .0373 |
| bsg | .28 | .0388 |
|  | .31 | .0271 |

Table 2 shows that the activity of ADP glucose pyrophosphorylase is not greatly reduced in the cotyledons of the present invention when compared to the activity in the variety Lazor.

TABLE 1

Starch and Sucrose Levels in Leaves from Lazor and *bsg*-introgressed lines of *Pisum sativum*

|  | Starch % dry wt | Starch % fresh wt | Sucrose % dry wt | Sucrose % fresh wt |
|---|---|---|---|---|
| Lazor | 3.060 +/− 0.071 | 0.4948 +/− 0.0220 | 8.18 +/− 0.69 | 1.32 +/− 0.14 |
| bsg | 0.015 +/− 0.002 | 0.0023 +/− 0.0004 | 10.19 +/− 0.78 | 1.58 +/− 0.12 |

Analysis of Phosphoglucomutase Isozymes by Starch Gel Electrophoresis

Embryos (0.25–0.3 g) or leaves (0.5 g) frozen in liquid nitrogen were ground in an ice-cold mortar in the presence of extraction buffer (0.1 M Tris-Cl, pH 7.8; 2% reduced glutatione) plus 50 mg of polyvinylpolypyrrolidone and a small amount of acid-washed sand. Extracts were squeezed through one layer of miracloth and, in some experiments, diluted with extraction buffer to equal chlorophyll concentrations (as determined by the formula: $[(A_{645} \times 202) + (A_{663} \times 80.2)] \times 10.5 = \mu g$ chlorophyll/ml). Extracts were taken up by 5 mm×1 cm 3MM wicks and placed 4 cm from the cathodal end in a 12% starch gel prepared in 15 mM Tris/4 mM citric acid, pH 7.8. A 3MM wick was used to connect the starch gel to the electrode buffer (0.3 M sodium borate, pH 7.8). Electrophoresis was done in the cold room for 20 minutes at 200 V/30 mA. The wicks were then removed and electrophoresis was continued at 30 mA until the voltage reached 300 V; the voltage was then maintained at 300 V until the dye front had moved ~11 cm.

The upper portion of the starch gel was then sliced off and the bottom 1 mm section was stained for phosphoglucomutase (PGM) activity using a 0.7% agarose overlay containing 0.1 M Tris-Cl (pH 7.5), 10 mM $MgCl_2$, 1.5 mg/ml glucose-1-P, 0.15 mg/ml NADP+, 0.2 mg/ml MTT, 40 $\mu$g/ml PMS, and 0.4 U/ml glucose-6 phosphate dehydrogenase. After a 15 minute incubation in the dark at 30° C., the gel was washed for 1 minute in 1% acetic acid, rinsed several times with water, and fixed in 5:2:1:4 ethanol:acetic:acid:glycerine water.

Figure 4:
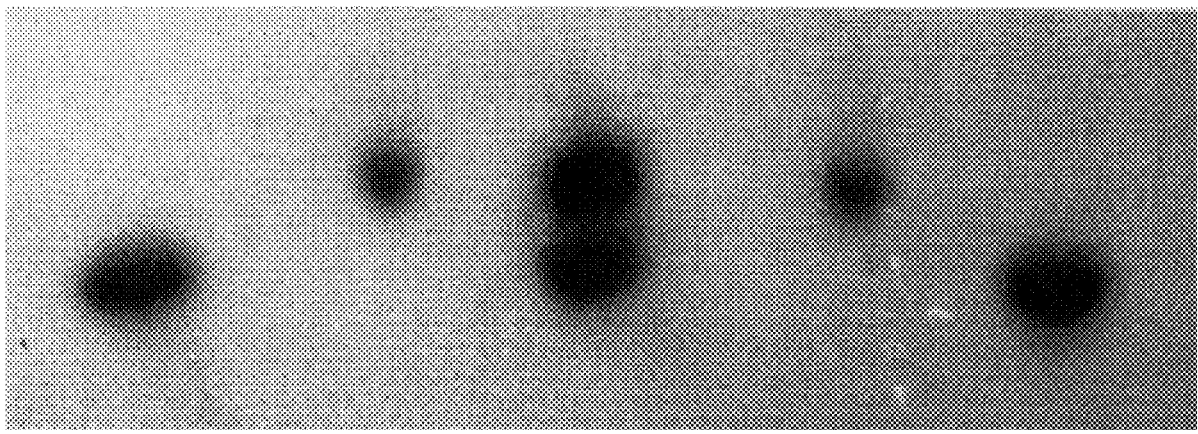
FIG. 4 shows the electrophoretic separation of phosphoglucomutase enzymes from a pea variety containing the *r* gene holozygous within its genome and from a *Pisum sativum* variety containing the *bsg* gene homozygous within its genome. Lane 1 shows leaf extract from a variety containing the *bsg* gene. Lane 2 shows chloroplasts isolated from a variety containing the *r* gene. Lane 3 shows leaf extract from a variety containing the *r* gene. Lane 4 shows chloroplasts isolated from a variety containing the *r* gene. Lane 5 shows leaf extract from a variety containing the *bsg* gene.
Figure 5:
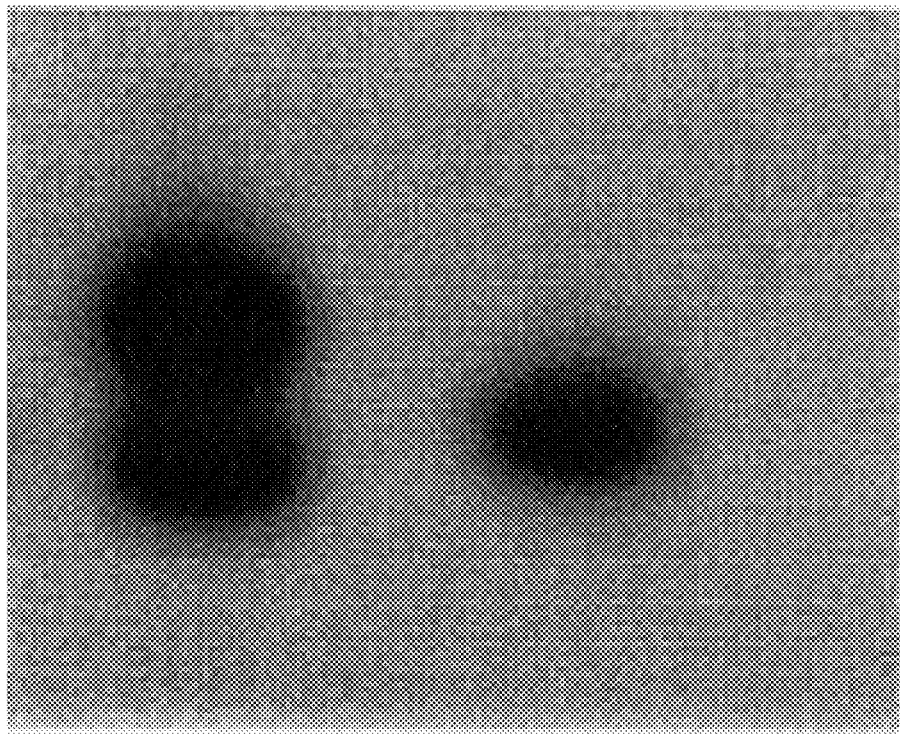
FIG. 5 shows an electrophoretic separation of phosphoglucomutase enzymes from peas containing the *r* gene and from peas containing the *bsg* gene. Lane 1 shows a cotyledon extract from a variety containing the *r* gene. Lane 2 shows a cotyledon extract from a variety containing the *bsg* gene.

FIG. 4 shows the electrophorectic separation of phosphoglucomutase isozymes in Lazor and in the *Pisum sativum* line having the *bsg* gene introgressed into Lazor. In Lazor, two isozymes are resolved in extracts from its leaves, whereas only one isozyme stains for phosphoglucomutase isozymes in the *bsg* gene introgressed *Pisum sativum* line of Lazor. In extracts from leaves from the *bsg* introgressed line of Lazor, the isozyme missing from the *bsg*-introgressed *Pisum sativum* line of Lazor, which is the less electronegative isozyme, is the isozyme found in isolated chloroplasts. The same isozyme band is also missing in embryo extracts from the *bsg*-introgressed *Pisum sativum* line of Lazor which is shown in FIG. 5.

Isolation of Chloroplasts

Chloroplasts were isolated according to the method described in *Methods in Plant Molecular Biology*, 141–172, Cold Spring Harbor Press, Lamppa, J. K., et al., eds. 1995, "Section 8 In vitro Import of Proteins into Chloroplasts," 1995, herein incorporated by reference. Leaves (~20 g) were gently homogenized in 450 ml of ice-cold grinding buffer (2 mM EDTA, 1 mM $MgCl_2$, 1 mM $MnCl_2$, 50 mM HEPES-KOH (pH 7.5), 0.33 M sorbitol) with a Polytron set at 3.5 for 2 one minute bursts. The homogenate was filtered through four layers of cheesecloth and four layers of Miracloth and then pelleted in a GSA rotor at 4000 rpm for 1 minute at 4° C. The pellets were resuspended in 8 ml of grinding buffer and layered over two 40%/80% Percoll step gradients made up in grinding buffer plus 0.86 mg/ml ascorbic acid and 0.35 mg/ml reduced glutathione. The gradients were spun in an HB-4 rotor at 7500 rpm for 8 minutes at 4° C. The lower chloroplast band was resuspended in 30 ml grinding buffer and repelleted by centrifugation in an HB-4 rotor at 3500 rpm for 5 minutes. The pellets were resuspended in 30 ml of 1×HSM (10 mM HEPES-KOH, pH 8, 0.33 M sorbitol, 8.4 mM methionine) and repelleted in an HB-4 rotor at 3500 rpm for 5 minutes at 4° C. The pellets were then either lysed by being taken up in hypotonic medium (10 mM Tris-Cl, pH 7.8, 2% reduced glutathione) or resuspended in 1×HSM and lysed by freeze-thawing.

EXAMPLE 3

Sugar Analysis of Frozen Peas

Peas of a *bsg* introgressed line, derived from crosses with Encore and referred to as Encore *BSG*, and peas of the *Pisum sativum* variety XPF330 were frozen for high performance liquid chromatography (HPLC). XPF330 is a proprietary variety of Seminis Vegetable Seeds, Inc. XPF330 is late season, produces wrinkled mature seed that contains the *r* gene and is resistant to Powdery Mildew Fungus. The frozen pea samples were stored at −20 degrees centigrade until extracted. The peas were subsampled and weighed out on a Mettler AT200 analytical balance. Absolute ethanol was added to the subsample (4:1 ratio, volume/weight). The sample was cooled and stored overnight (at −20° C.) then ground with an IKA Ultra Turrax T25 homogenizer. The homogenate was returned to the freezer. The following day, the sample was mixed, then centrifuged to clarify the extract. An aliquot was removed and sealed in an autosampler vial and stored at −20° C. until analyzed.

The sugars are separated on a Hewlett-Packard 1050 HPLC chemstation system, employing a refractive index detector. The column used was a Whatman Partsil 5PAC column (4×12.5 mm). The solvent system was composed of 85% acetonitrile at a flow rate of 0.85 ml/minute at 35° C. The injection volume was 5 microliters. A standard mixture of glucose, fructose and sucrose in 80% ethanol was used to quantitate the sugars. This standard was injected after every tenth sample. The results are shown below in Table 3.

TABLE 3

| LINE | | Fru | Glc | Suc |
|---|---|---|---|---|
| Encore BSG | Avg. | 0.058 | 0.031 | 6.773 |
| | Stds | 0.008 | 0.011 | 0.271 |
| | CV | 14.451 | 33.973 | 4.001 |
| | StdErr | 0.003 | 0.004 | 0.111 |
| | Count | 6 | | |
| XPF330 | Avg. | 0.037 | 0.019 | 4.552 |
| | Stds | 0.003 | 0.004 | 0.125 |
| | CV | 7.884 | 22.959 | 2.757 |
| | StdErr | 0.001 | 0.002 | 0.051 |
| | Count | 6 | | |

The results shown above in Table 3 demonstrate that peas containing the *bsg* gene homozygous within their genome contain higher levels of fructose, glucose and sucrose than peas containing the *r* gene homozygous within its genes.

EXAMPLE 4

Sucrose Analysis of Frozen Peas

Frozen samples from the *Pisum sativum* varieties or lines listed below in Tables 4 and were stored at −20° C. until extracted. The peas were subsampled and weighed out on a Mettler AT200 analytical balance. Absolute ethanol was added to the subsample (4:1 ratio, volume/weight). The sample was cooled and stored overnight (at −20° C.) then ground with an IKA Ultra Turrax T25 homogenizer. The homogenate was returned to the freezer. The following day, the sample was mixed, then centrifuged to clarify the extract. An aliquot was removed and sealed in an autosampler vial and sealed in an autosampler vial and stored at −20° C. until analyzed.

The sugars are separated on a Hewlett-Packard 1050 HPLC chemstation system, employing a refractive index detector. The column used was a Whatman Partsil 5PAC column (4×12.5 mm). The solvent system was composed of 85% acetonitrile at a flow rate of 0.85 ml/minute at 35° C. The injection volume was 5 microliters. A standard mixture of sucrose in 80% ethanol was used to quantitate sucrose. This standard was injected every tenth sample. The results are shown below in Tables 4 and 5.

TABLE 4

(fresh weight)

| Variety | Tenderometer | % Sucrose Average | bsg gene |
|---|---|---|---|
| Bolero | 99 | 4.75 | No |
| Bolero | 99 | 4.64 | No |
| Dual | 97 | 4.56 | No |
| Dual | 97 | 4.27 | No |
| EX 8500567 | 95 | 6.26 | Yes |
| EX 8500567 | 95 | 6.22 | Yes |
| EX 8500567 | 102 | 6.39 | Yes |
| EX 8500567 | 102 | 6.40 | Yes |
| Lazor | 93 | 4.78 | No |
| Lazor | 93 | 5.06 | No |
| Lazor | 99 | 4.82 | No |
| Lazor | 99 | 4.89 | No |
| Lazor *BSG* | 95 | 6.37 | Yes |
| Lazor *BSG* | 95 | 6.50 | Yes |
| Lazor *BSG* | 97 | 6.45 | Yes |
| Lazor *BSG* | 97 | 6.56 | Yes |
| Quantum | 98 | 4.82 | No |
| Quantum | 98 | 4.83 | No |
| Spring | 98 | 4.86 | No |
| Spring | 104 | 4.77 | No |
| Tacoma | 94 | 4.78 | No |
| Tacoma | 94 | 4.72 | No |
| Tacoma | 99 | 4.47 | No |
| Tacoma | 99 | 4.39 | No |
| XP F357 | 96 | 5.15 | No |
| XP F357 | 96 | 5.57 | No |
| XP F357 | 104 | 5.36 | No |
| XP F357 | 104 | 5.31 | No |

TABLE 5

Sucrose Analysis of Frozen Peas (fresh weight)

| Variety | % Sucrose Average | Tenderometer | bsg gene |
|---|---|---|---|
| BIR X MCRO | 4.90 | 97 | No |
| BEMAf x Alf | 4.81 | 100 | No |
| Bolero | 5.25 | 96 | No |
| Bolero x Bemol Af | 4.75 | 98 | No |
| CM279 | 5.52 | 102 | No |
| CM279 | 5.45 | 98 | No |
| CM279 | 5.57 | 98 | No |
| CM279 | 5.02 | 100 | No |
| Dinos | 4.74 | 97 | No |
| 8500567 | 6.59 | 96 | Yes |
| 8500567 | 7.06 | 97 | Yes |
| 8500567 | 6.70 | 90 | Yes |
| 8500567 | 5.75 | 87 | Yes |
| EF680 X Tacoma | 4.83 | 104 | No |
| Encore X Tacoma | 4.79 | 98 | No |
| F226 X Darfon | 4.61 | 103 | No |
| F234 X Mrkd | 5.73 | 103 | No |
| F240 X Tacoma | 5.16 | 97 | No |
| F240 X Tacoma | 4.90 | 98 | No |
| F353 | 5.50 | 99 | No |
| F357 | 5.11 | 97 | No |
| F383 | 5.38 | 97 | No |
| Kalamo | 5.09 | 97 | No |
| Lazor | 5.61 | 100 | No |
| Lazor | 5.31 | 97 | No |
| Lazor | 5.25 | 97 | No |
| Lazor *BSG* | 7.10 | 92 | Yes |
| Lazor *BSG* | 7.07 | 95 | Yes |
| Lazor *BSG* | 6.74 | 93 | Yes |
| Lea X F240 | 5.86 | 97 | No |
| Lea X Tacoma | 5.18 | 103 | No |
| M153 | 4.84 | 97 | No |
| Micro PMB Cl | 4.88 | 97 | No |
| Novll X F240 | 5.06 | 101 | No |
| PlSdin X Nvll | 5.42 | 100 | No |
| PlSDn X Nvll | 6.08 | 97 | No |
| Sknd X R86275 X Nv | 5.13 | 102 | No |
| Sknd X R86275 X Nv | 5.51 | 98 | No |
| Snake | 5.09 | 98 | No |
| Spr DMBC X R90172 | 5.85 | 98 | No |
| Spring | 5.34 | 95 | No |
| Spring | 5.20 | 99 | No |
| Spring | 4.78 | 96 | No |

The *Pisum sativum* varieties, Bolero, Dual, Lazor, Quantum, Spring and Tacoma listed in Table 4, produce wrinkled mature seeds and contain *r* gene homozygous within their genome. These varieties are commercially available from Seminis Vegetable Seeds, Inc. The *Pisum sativum* varieties 8500567 and 8500557, also shown in Table 4, produce highly wrinkled seeds and contain the *bsg* gene homozygous within their genome. 8500567 and 8500557 are proprietary varieties of Seminis Vegetable Seeds, Inc. The *Pisum sativum* line, Lazor *BSG* also shown in Table 4, produces highly wrinkled seeds and contains the *bsg* gene homozygous within its genome. Lazor *BSG* is a proprietary variety of Seminis Vegetable Seeds, Inc. XPF357, also shown in Table 4, produces wrinkled seeds and contains the *r* gene within its genome. XPF357 is a proprietary variety of Seminis Vegetable Seeds, Inc.

The *Pisum sativum* varieties and breeding lines shown in Table 5, with the exception of 8000567 and Lazor *BSG*, produce wrinkled seeds and contain the *r* gene homozygous within their genome. All of these varieties (with the exception of Snake) are proprietary varieties (or breeding lines) of Seminis Vegetable Seeds, Inc. The *Pisum sativum* varieties Bolero, Lazor, Dinos, Kalamo and Spring, produce wrinkled seeds and contain the *r* gene homozygous within their genome. These varieties are commercially available from Seminis Vegetable Seeds, Inc.

Snake, also shown in Table 6, produces wrinkled seeds and contains the *r* gene homozygous within its genome. Snake is commercially available from Cristes Moscow Growers, Moscow, Id.

The average sucrose produced by peas containing the *bsg* gene homozygous in its genome in Tables 4 and 5 was 6.54 (with values ranging from 5.75 to 7.10 when measured at tenderometer values from about 87 to about 102). The average amount of sucrose produced by peas that did not contain the *bsg* gene in the sucrose tests conducted in 1996–1997 was 5.08 (with values ranging from 4.27 to 6.08).

EXAMPLE 5

Alcohol Insoluble Solids Analysis in Various Peas

This Example describes the alcohol insoluble solids content on canned peas from several different *Pisum sativum* varieties or lines. The protocol for determining the alcohol insoluble solids on these canned peas is as follows:

a) open can, pour the contents over an 8 mesh sieve, rinse with two volumes of tap water, and allowed to drain for two (2) minutes;

b) weigh 90–100 grams of peas to the nearest 0.1 gram, transfer to a blender cup, add to the cup an equal volume of deionized water;

c) blend the peas for two (2) minutes on the blend setting;

d) weigh 40 grams of the blended mix to the nearest 0.01 grams and transfer quantitatively to a 1 liter boiling flask fitted with a reflux condenser. 280 ml of 86% ethanol is used to complete the transfer;

e) boil the mixture for 30 minutes;

f) place a 11 cm Whatman #1 filter paper, previously dried in a metal weighing dish and weighed to the nearest 0.01 grams, into an 8 cm Buchner filter apparatus, in a manner so that the edges of the paper extend 1 cm up the sides of the filter apparatus. Apply suction to the apparatus and filter the alcohol-solids mixture quantitatively through the paper; wash the residue from the flask with 80% ethanol until the washings are colorless. Do not overfill the cup formed by the filter paper; and g) return the filter paper to a drying oven in its original metal weighing dish and dry at 100° C. for 2 hours. Cool in a desiccator and weigh to the nearest 0.01 grams. Determine the weight of dry, alcohol insoluble solids by difference and multiply by 5 to convert to percentage alcohol insoluble solids.

The alcohol insoluble solids value at 105 tenderometer was calculated using linear regression from paired measures of alcohol insoluble solids and tenderometer for each variety. The tenderometer value at 12% alcohol insoluble solids was calculated by linear regression from the same paired data. For the pea varieties of the present invention that contain the *bsg* gene, it was necessary to extend the regression line beyond the range of data in order to intercept 12 percent. For example, 8500557, a pea variety containing the *bsg* gene, had 7.2% AIS at a tenderometer of 105, and the calculated tenderometer for 12% AIS is 199. Table 6, below shows the alcohol insoluble solids value at 105 and 12.0 tenderometer for several varieties of *Pisum sativum*.

TABLE 6

| Code | Tdr= | 105 | AIS= | 12.0 | bsg gene |
|---|---|---|---|---|---|
| 8500557 | AIS= | 7.2 | Tdr= | 199 | Yes |
| 8500567 | AIS= | 7.7 | Tdr= | 200 | Yes |
| Tender | AIS= | 8.9 | Tdr= | 124 | No |
| Revolution | AIS= | 9.3 | Tdr= | 135 | No |
| 10 002 | AIS= | 9.8 | Tdr= | 127 | No |
| 20 028 | AIS= | 10.1 | Tdr= | 128 | No |
| Zamira | AIS= | 10.2 | Tdr= | 123 | No |
| Pacha | AIS= | 10.3 | Tdr= | 126 | No |
| Cabro | AIS= | 10.3 | Tdr= | 124 | No |
| 20 037 | AIS= | 10.3 | Tdr= | 124 | No |
| CMG290 | AIS= | 10.4 | Tdr= | 123 | No |
| Magic | AIS= | 10.4 | Tdr= | 119 | No |
| Avola | AIS= | 10.4 | Tdr= | 125 | No |
| 20 036 | AIS= | 10.5 | Tdr= | 124 | No |
| Fresca | AIS= | 10.5 | Tdr= | 121 | No |
| 10 003 | AIS= | 10.5 | Tdr= | 122 | No |
| Bolero | AIS= | 10.5 | Tdr= | 120 | No |
| Samish | AIS= | 10.6 | Tdr= | 121 | No |
| Quad | AIS= | 10.6 | Tdr= | 119 | No |
| Titan | AIS= | 10.6 | Tdr= | 121 | No |
| 20 029 | AIS= | 10.7 | Tdr= | 114 | No |
| Renard | AIS= | 11.0 | Tdr= | 116 | No |
| 20 047 | AIS= | 11.1 | Tdr= | 115 | No |
| 20 019 | AIS= | 11.3 | Tdr= | 119 | No |
| Methow | AIS= | 11.5 | Tdr= | 110 | No |

TABLE 6-continued

| Code | Tdr= | 105 | AIS= | 12.0 | bsg gene |
|---|---|---|---|---|---|
| 20 035 | AIS= | 11.8 | Tdr= | 107 | No |
| Catalina | AIS= | 12.0 | Tdr= | 105 | No |
| Fristo | AIS= | 12.0 | Tdr= | 105 | No |
| Orlando | AIS= | 13.2 | Tdr= | 95 | No |
| Kong | AIS= | NS | Tdr= | NS | No |
| Lazor *BSG*BC1 | AIS= | 8.0 | Tdr= | 194 | Yes |
| Lazor *BSG*BC2 | AIS= | 8.4 | Tdr= | 180 | Yes |
| 20 078 | AIS= | 8.7 | Tdr= | 131 | No |
| Paso | AIS= | 9.0 | Tdr= | 133 | No |
| Mathilde | AIS= | 9.1 | Tdr= | 131 | No |
| 20 071 | AIS= | 9.3 | Tdr= | 125 | No |
| 20 089 | AIS= | 9.5 | Tdr= | 128 | No |
| Globo | AIS= | 9.5 | Tdr= | 124 | No |
| 20 091 | AIS= | 9.6 | Tdr= | 121 | No |
| Waverex | AIS= | 9.6 | Tdr= | 131 | No |
| 20 067 | AIS= | 9.7 | Tdr= | 129 | No |
| 20 100 | AIS= | 9.8 | Tdr= | 122 | No |
| 20 101 | AIS= | 9.9 | Tdr= | 123 | No |
| 20 092 | AIS= | 10.0 | Tdr= | 127 | No |
| 10 021 | AIS= | 10.0 | Tdr= | 121 | No |
| 10 025 | AIS= | 10.1 | Tdr= | 126 | No |
| 20 090 | AIS= | 10.2 | Tdr= | 125 | No |
| Nitro | AIS= | 10.2 | Tdr= | 123 | No |
| 10 016 | AIS= | 10.2 | Tdr= | 123 | No |
| 20 075 | AIS= | 10.3 | Tdr= | 124 | No |
| 10 015 | AIS= | 10.3 | Tdr= | 125 | No |
| Darfon | AIS= | 10.3 | Tdr= | 120 | No |
| Kimo | AIS= | 10.4 | Tdr= | 123 | No |
| 20 093 | AIS= | 10.4 | Tdr= | 121 | No |
| R555 | AIS= | 10.4 | Tdr= | 127 | No |
| 20 068 | AIS= | 10.4 | Tdr= | 121 | No |
| 20 030 | AIS= | 10.4 | Tdr= | 122 | No |
| Barle | AIS= | 10.5 | Tdr= | 119 | No |
| 20 069 | AIS= | 10.5 | Tdr= | 117 | No |
| 10 020 | AIS= | 10.5 | Tdr= | 121 | No |
| Brule | AIS= | 10.6 | Tdr= | 118 | No |
| 20 073 | AIS= | 10.7 | Tdr= | 119 | No |
| Curico | AIS= | 10.7 | Tdr= | 115 | No |
| Purser | AIS= | 10.7 | Tdr= | 115 | No |
| 20 094 | AIS= | 10.7 | Tdr= | 120 | No |
| 20 116 | AIS= | 10.7 | Tdr= | 117 | No |
| 20 076 | AIS= | 10.8 | Tdr= | 119 | No |
| Lynx | AIS= | 10.9 | Tdr= | 115 | No |
| 20 102 | AIS= | 10.9 | Tdr= | 118 | No |
| 20 103 | AIS= | 10.9 | Tdr= | 118 | No |
| Sigra | AIS= | 10.9 | Tdr= | 116 | No |
| Encore | AIS= | 11.0 | Tdr= | 115 | No |
| Alamado | AIS= | 12.0 | Tdr= | 115 | No |
| Markado | AIS= | 11.0 | Tdr= | 116 | No |
| 20 070 | AIS= | 11.1 | Tdr= | 115 | No |
| Bolero | AIS= | 11.1 | Tdr= | 114 | No |
| Spring | AIS= | 11.1 | Tdr= | 114 | No |
| Tyne | AIS= | 11.1 | Tdr= | 116 | No |
| Deltafon | AIS= | 11.2 | Tdr= | 111 | No |
| 10 017 | AIS= | 11.2 | Tdr= | 113 | No |
| Wolf | AIS= | 11.2 | Tdr= | 113 | No |
| 20 119 | AIS= | 11.3 | Tdr= | 111 | No |
| Lazor | AIS= | 11.4 | Tdr= | 110 | No |
| 20 063 | AIS= | 11.4 | Tdr= | 110 | No |
| 20 074 | AIS= | 11.4 | Tdr= | 113 | No |
| 20 087 | AIS= | 11.4 | Tdr= | 113 | No |
| Camina | AIS= | 11.4 | Tdr= | 112 | No |
| 20 120 | AIS= | 11.4 | Tdr= | 112 | No |
| Masterfon | AIS= | 11.5 | Tdr= | 111 | No |
| 20 118 | AIS= | 11.5 | Tdr= | 110 | No |
| Vevas | AIS= | 11.5 | Tdr= | 110 | No |
| 20 106 | AIS= | 11.6 | Tdr= | 107 | No |
| Snake | AIS= | 11.6 | Tdr= | 109 | No |
| 20 088 | AIS= | 11.7 | Tdr= | 108 | No |
| 20 117 | AIS= | 11.8 | Tdr= | 107 | No |
| 20 072 | AIS= | 11.9 | Tdr= | 106 | No |
| Prism | AIS= | 12.0 | Tdr= | 105 | No |
| Dual | AIS= | 13.0 | Tdr= | 95 | No |

The *Pisum sativum* varieties Tender, Revolution, Avola, Orlando, Markado, Barle, Sigra, Encore, Methow, Alamado, Tyne, Deltafon, Lazor, Camina, Wolf, Masterfon, Veras, Pacha, Bolero, Cabro, Fristo, Paso, Mathilde, Globe, Nitro, Darfon, Kimo, Dual, Prism, Magic, Titan, Renard, Catalina, Kong, Curico and Lynx listed in Table 6, produce wrinkled mature seeds and contain the *r* gene homozygous within their genome. These varieties are commercially available from Seminis Vegetable Seeds, Inc. The *Pisum sativum* varieties CMG290, Samish, Quad, Snake and Brule produce wrinkled seed and contain the *r* gene homozygous within their genome. These *Pisum sativum* varieties are commercially available from Crites Moscow Growers, Moscow, Id.

The *Pisum sativum* variety Zamira produces wrinkled mature seeds and contains the *r* gene homozygous within its genome. Zamira is commercially available from Nunhems Zaden (Haelen, Netherlands).

The *Pisum sativum* variety Fresca produces wrinkled mature seeds and contains the *r* gene homozygous within its genome. Fresca is commercially available from Vilmoran (Empire, Calif.).

The *Pisum sativum* variety Waverex produces wrinkled mature seeds and contains the r gene homozygous within its genome. Waverex is commercially available from Van Waveren (Gottingen, West Germany).

The *Pisum sativum* variety Purser produces wrinkled mature seeds and contains the *r* gene homozygous within its genome. Purser is commercially available from Novartis (Boise, Id.).

The *Pisum sativum* varieties 8500557 and 8500567 produce highly wrinkled mature seeds and contains the *bsg* gene homozygous within their genome. 8500557 and 8500567 are proprietary varieties of Seminis Vegetable Seeds.

All other *Pisum sativum* varieties or lines used in Table 6 produce wrinkled mature seeds and contains the *r* gene homozygous within their genome. All are proprietary varieties of Seminis Vegetable Seeds, Inc.

EXAMPLE 6

Analysis of Sucrose and AIS Levels 22 frozen samples of peas were tested for the percentage (%) sucrose and alcohol insoluble solids. Peas were tested from the *Pisum sativum* varieties or lines Quantum, Lazor and Lazor *BSG*BC2. Lazor *BSG*BC2 was selected after 2 back crosses of the *bsg* from M82.1 into Lazor (as a recurrent parent). The same procedures used in Examples 3 and 4 to determine and AIS were used in this Example. The results are shown in Table 7.

TABLE 7

| Variety | Tenderometer | % Sucrose | % AIS |
| --- | --- | --- | --- |
| Quantum | 92 | 6.01 | 8.8 |
| Quantum | 100 | 6.26 | 9.6 |
| Lazor | 95 | 5.88 | 9.5 |
| Lazor | 101 | NA | 10.7 |
| Lazor *BSG*BC2 | 91 | 7.01 | 7.3 |
| Lazor *BSG*BC2 | 99 | 7.07 | NA |

These results show that peas of the *Pisum sativum* line Lazor *BSG*BC2 contained a higher percentage fresh weight of sucrose and lower % of AIS than the Quantum and Lazor varieties.

What is claimed is:

1. A *Pisum sativum* variety comprising a *bsg* gene in a homozygous state within its genome, wherein said *Pisum sativum* variety produces peas which contain the *bsg* gene.

2. The *Pisum sativum* variety of claim 1 wherein the peas contain from about 6.0 to about 7.5 percent fresh weight sucrose when measured at a tenderometer value of from about 90 to about 110 and from about 6.5 to about 8.0 percent by weight of alcohol insoluble solids when measured at a tenderometer value of about 105.

3. The *Pisum sativum* variety of claim 1 wherein the peas contain about 20% less alcohol insoluble solids than seeds produced from a *Pisum sativum* variety that does not contain the *bsg* gene within its genome.

4. The *Pisum sativum* variety of claim 1, wherein the *Pisum sativum* variety containing the *bsg* gene is resistant to Fusarium Wilt Fungus and Powdery Mildew Fungus.

5. The *Pisum sativum* variety of claim 1 wherein the peas contain from about 5 percent fresh weight to about 30 percent fresh weight more sucrose than seeds produced from a *Pisum sativum* variety that does not contain the *bsg* gene within its genome.

6. The *Pisum sativum* variety of claim 5 wherein the peas contain from about 10 percent fresh weight to about 20 percent fresh weight more sucrose than peas produced from a *Pisum sativum* variety containing the *r* gene within its genome.

7. A *Pisum sativum* variety grown from seed having ATCC Accession No. 209425 comprising a *bsg* gene in a homozygous state within its genome and which produces peas which contain the *bsg* gene and further comprises from about 6.0 to about 7.5 percent fresh weight sucrose when measured at a tenderometer value of from about 90 to about 110 and from about 6.5 to about 8.0 percent by weight alcohol insoluble solids when measured at a tenderometer value of about 105.

8. Peas from a *Pisum sativum* variety comprising a *bsg* gene in a homozygous state within its genome and which further contain from about 6.0 to about 7.5 percent fresh weight sucrose when measured at a tenderometer value of from about 90 to about 110 and from about 6.5 to about 8.0 percent weight alcohol insoluble solids when measured at a tenderometer value of about 105.

9. A *Pisum sativum* plant grown from the peas of claim 8.

10. A process for producing peas that contain higher levels of sucrose and lower levels of alcohol insoluble solids than peas produced from a *Pisum sativum* variety that does not contain the *bsg* gene, the process comprising the steps of: crossing a *Pisum sativum* variety or line that contains the *bsg* gene within its genome with a *Pisum sativum* variety or line that does not contain the *bsg* gene within its genome; collecting mature seeds; planting the collected mature seeds; growing the mature seeds into *Pisum sativum* plants; allowing the plants to self-pollinate; collecting mature seeds; selecting highly wrinkled mature seeds that do not contain organized starch grains; planting the selected mature seeds; growing the mature seeds into *Pisum sativum* plants; selecting plants with desirable phenotypic traits; allowing the plants to self-pollinate until a uniform *Pisum sativum* line is produced; allowing the line to self-pollinate; collecting the resulting peas.

11. The process of claim 10 wherein the peas contain from about 6.0 to about 7.5 percent fresh weight sucrose when measured at a tenderometer value of from about 90 to about 110 and from about 6.5 to about 8.0 percent by weight alcohol insoluble solids when measured at a tenderometer value of about 105.

12. The process of claim 10 wherein the *Pisum sativum* variety that does not contain the *bsg* gene within its genome contains a *r* gene within its genome that produces wrinkled mature seeds.

13. The process of claim 10 wherein the *Pisum sativum* variety that does not contain the *bsg* gene within its genome contains a *rb* gene within its genome.

14. The process of claim 10 wherein the *Pisum sativum* variety that does not contain the *bsg* gene within its genome contains the *R* gene within its genome.

15. A process for producing peas that contain higher levels of sucrose and lower levels of alcohol insoluble solids than peas produced from a *Pisum sativum* variety that does not contain the *bsg* gene, the process comprising the steps of: crossing a *Pisum sativum* variety or line that contains the *bsg* gene within its genome with a second *Pisum sativum* variety or line that contains the *bsg* gene within its genome; collecting mature seeds; planting the collected mature seeds; growing the mature seeds into *Pisum sativum* plants; selecting *Pisum sativum* plants with desirable phenotypic traits; allowing the plants to self-pollinate until a uniform line is produced; allowing the line to self-pollinate; and collecting the resulting peas.

16. The process of claim 15 wherein the peas contain from about 6.0 to about 7.5 percent fresh weight sucrose when measured at a tenderometer value of from about 90 to about 110 and from about 6.5 to about 8.0 percent by weight alcohol insoluble solids when measured at a tenderometer value of about 105.

17. A process for producing peas that contain from about 6.0 to about 7.5 percent fresh weight sucrose when measured at a tenderometer value of from about 90 to about 110 and from about 6.5 to about 8.0 percent by weight alcohol insoluble solids when measured at a tenderometer value of about 105, the process comprising the steps of: crossing a *Pisum sativum* variety or line that contains the *bsg* gene within its genome with a *Pisum sativum* variety or line that does not contain the *bsg* gene within its genome; collecting mature seeds; planting the mature seeds; growing the mature seeds into a *Pisum sativum* plants; allowing the plants to self-pollinate; collecting mature seeds; selecting highly wrinkled mature seeds that do not contain any organized starch grains; planting the selected mature seeds; growing the mature seeds into *Pisum sativum* plants; selecting plants with desirable phenotypic traits; allowing the plants to self-pollinate until a uniform line is produced; allowing the line to self-pollinate; and collecting the resulting peas.

18. A process for producing peas of a *Pisum sativum* variety that contain from about 6.0 to about 7.5 percent fresh weight sucrose when measured at a tenderometer value of from about 90 to about 110 and from about 6.5 to about 8.0 percent by weight alcohol insoluble solids when measured at a tenderometer value of about 105, the process comprising the steps of: crossing a *Pisum sativum* variety or line that contains the *bsg* gene within its genome with a second *Pisum sativum* variety or line that contains the *bsg* gene within its genome; collecting mature seeds; planting the collected mature seeds; growing the mature seeds into *Pisum sativum* plants; selecting *Pisum sativum* plants with desirable phenotypic traits; allowing the plants to self-pollinate until a uniform *Pisum sativum* line is produced; allowing the line to self-pollinate; and collecting the resulting peas.

19. A process of producing highly wrinkled mature seed of a *Pisum sativum* variety that contains the *bsg* gene within its genome, the process comprising the steps of: crossing a *Pisum sativum* variety or line that contains the *bsg* gene within its genome with a second *Pisum sativum* variety or line that contains the *bsg* gene within its genome; and collecting the resulting mature seeds.

20. A *Pisum sativum* plant grown from the highly wrinkled seed of claim 19.

21. Peas harvested from the plant grown in claim 20.

22. A process of producing highly wrinkled mature seed of a *Pisum sativum* variety that contains the *bsg* gene within its genome, the process comprising the steps of: crossing a *Pisum sativum* variety or line that contains the *bsg* gene within its genome with a *Pisum sativum* variety or line that does not contain the *bsg* gene within its genome; collecting mature seeds; planting the collected mature seeds; growing the mature seeds into *Pisum sativum* plants; allowing the *Pisum sativum* plants to self-pollinate; collecting mature seeds; selecting highly wrinkled mature seeds that do not contain organized starch grains, growing the mature seeds into *Pisum sativum* plants, selecting plants with desirable phenotypic traits; allowing the plants to self-pollinate until a uniform line is produced; allowing the *Pisum sativum* line to self-pollinate; and collecting the mature seeds.

23. A *Pisum sativum* plant grown from highly wrinkled seed of claim 22.

* * * * *